United States Patent
Merryman et al.

(10) Patent No.: US 9,226,787 B2
(45) Date of Patent: Jan. 5, 2016

(54) CATHETER HAVING TEMPERATURE CONTROLLED ANCHOR AND RELATED METHODS

(75) Inventors: William David Merryman, Nashville, TN (US); H. Thomas McElderry, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 875 days.

(21) Appl. No.: 13/384,148

(22) PCT Filed: Jul. 15, 2010

(86) PCT No.: PCT/US2010/042047
§ 371 (c)(1),
(2), (4) Date: Jun. 15, 2012

(87) PCT Pub. No.: WO2011/008903
PCT Pub. Date: Jan. 20, 2011

(65) Prior Publication Data
US 2013/0030424 A1    Jan. 31, 2013

Related U.S. Application Data

(60) Provisional application No. 61/225,641, filed on Jul. 15, 2009.

(51) Int. Cl.
| | |
|---|---|
| *A61B 18/02* | (2006.01) |
| *A61B 18/14* | (2006.01) |
| *A61B 18/18* | (2006.01) |
| *A61B 18/20* | (2006.01) |
| *A61B 18/00* | (2006.01) |
| *A61M 25/04* | (2006.01) |

(52) U.S. Cl.
CPC ............. *A61B 18/02* (2013.01); *A61B 18/1492* (2013.01); *A61B 18/1815* (2013.01); *A61B 18/20* (2013.01); *A61B 2018/00011* (2013.01); *A61B 2018/00279* (2013.01); *A61B 2018/00369* (2013.01); *A61B 2018/00642* (2013.01); *A61B 2018/00744* (2013.01); *A61B 2018/00791* (2013.01); *A61B 2018/0212* (2013.01); *A61B 2018/1861* (2013.01); *A61M 25/04* (2013.01)

(58) Field of Classification Search
CPC .......... A61B 18/02; A61B 2018/0262; A61B 18/1492; A61B 18/1815; A61B 18/20
USPC ......................................... 606/40, 41, 49, 23
See application file for complete search history.

(56) References Cited

U.S. PATENT DOCUMENTS

| 5,575,772 A | 11/1996 | Lennox |
| 7,288,092 B2 | 10/2007 | Hooven |

(Continued)

OTHER PUBLICATIONS

The International Search Report and The Written Opinion for PCT/US2010/042047 mailed Mar. 9, 2011.

*Primary Examiner* — Theodore Stigell
*Assistant Examiner* — Michael Carey
(74) *Attorney, Agent, or Firm* — Myers Bigel Sibley & Sajovec, PA

(57) ABSTRACT

A catheter includes a catheter body having a temperature-controlled anchor element thereon that is configured to attach the catheter body to tissue by forming a congealed adherence layer between the anchor element and the tissue. An ablation element is connected to the catheter body and is configured to ablate tissue when the anchor element is attached to the tissue.

14 Claims, 6 Drawing Sheets

(56) References Cited

U.S. PATENT DOCUMENTS

| | | |
|---|---|---|
| 7,303,554 B2 | 12/2007 | Lalonde |
| 7,303,560 B2 | 12/2007 | Chin |
| 7,393,350 B2 | 7/2008 | Maurice |
| 7,393,353 B2 | 7/2008 | Hooven |
| 7,449,018 B2 | 11/2008 | Kramer |
| 7,465,300 B2 | 12/2008 | Arless |
| 7,487,780 B2 | 2/2009 | Hooven |
| 2003/0153899 A1 | 8/2003 | Eshel |
| 2004/0236365 A1 | 11/2004 | Cioanta |
| 2005/0288730 A1* | 12/2005 | Deem et al. ............ 607/42 |
| 2007/0239138 A1 | 10/2007 | Lawrence |
| 2009/0005769 A1 | 1/2009 | Haywood |
| 2009/0036823 A1 | 2/2009 | LePivert |
| 2011/0082453 A1* | 4/2011 | Fischer .......... A61B 18/02 606/21 |

\* cited by examiner

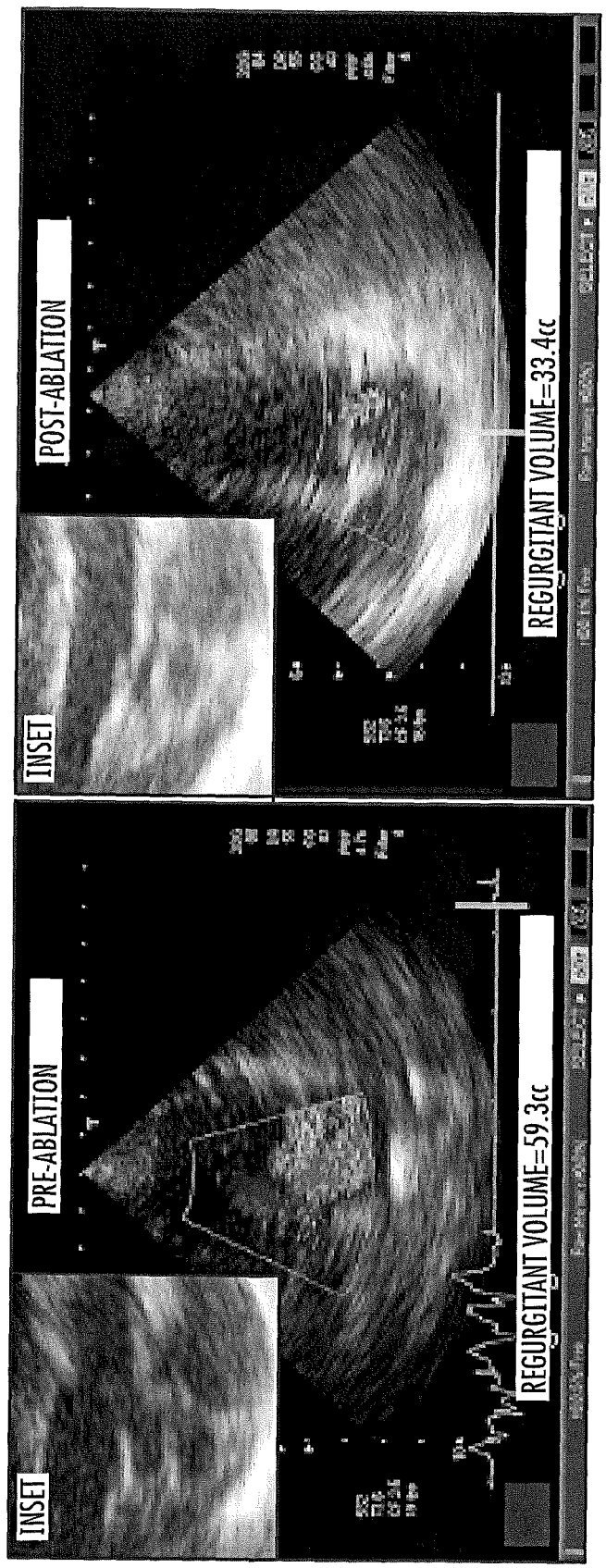

ly as International Publication No. WO 2011/008903 A2 on 20 Jan. 2011.

CATHETER HAVING TEMPERATURE CONTROLLED ANCHOR AND RELATED METHODS

RELATED APPLICATIONS

This application is a 35 U.S.C. §371 national stage application of PCT Application No. PCT/GB2010/042047, filed on Jul. 15, 2010, which claims priority from U.S. Provisional Application No. 61/225,641, filed on Jul. 15, 2009, the contents of which are incorporated herein by reference in their entireties. The above-referenced PCT International Application was published in the English language as International Publication No. WO 2011/008903 A2 on 20 Jan. 2011.

FIELD OF THE INVENTION

The present invention relates to catheters, and in particular, to catheter anchoring devices.

BACKGROUND

The mitral valve is a complex structure located between the left atrium and ventricle of the mammalian heart. During systole, large pressures (e.g., greater than 120 mmHg) are imposed on the closed mitral valve. The mitral valve leaflets resist these pressures to prevent mitral regurgitation, which can cause serious cardiac complications. The mitral valve includes two leaflets (anterior and posterior) whose free edges are tethered to the wall of the left ventricle at the papillary muscles via the chordae tendinae. The basal edges of the leaflets are attached to the left ventricle via a fibrous annular ring. The anterior leaflet is a single continuous membrane, and the posterior leaflet is made up of three scallops with the central scallop being the largest.

Although there are multiple components of the mitral valve complex that can lead to dysfunction, a loss of structural integrity of the mitral valve leaflets to withstand systolic pressure can be detrimental to mitral valve performance. A specific mitral valve syndrome called mitral valve prolapse occurs when the leaflets billow back into the left atrium during systole, typically resulting in compromised mitral valve and cardiac function. Cardiologic hallmarks of mitral valve prolapse include superior displacement, such as more than 2 mm, of one or both of the leaflets into the left atrium.

Clinically, there are two distinct patient groups with mitral valve prolapse. The first group is typically younger females, and the majority of this group do not require intervention. The second group is older males with moderate to severe mitral regurgitation and thickening leaflets. Histological analysis of autopsied mitral valve prolapse leaflets from this second patient group typically reveals disrupted and/or fragmented collagen architecture with enhanced quantity of proteogylcans. This disrupted architecture is called myxomatous mitral valve disease. Because of the disrupted architecture of the myxomatous mitral valve leaflets, collagen fibers are unable to provide the neaded structural integrity to appose left ventricle pressure during systole, and the leaflet(s) displaces into the atrium, prohibiting closure and leading to mitral regurgitation.

Standard treatments for myxomatous mitral valve disease are surgical repair or replacement. Both repair and replacement of the mitral valve are expensive, potentially invasive procedures with substantial recovery times. Percutaneous edge-to-edge repair procedures can be used in some cases of myxomatous mitral valve disease, which avoids open-chest surgery and reduces hospital stay and recovery time. However, the current mode of edge-to-edge repair has a significant detractor in that it can form a double-orifice mitral valve, and the long-term fluid mechanics and left ventricle remodeling of this flow pattern are not well-understood. Moreover, if the degree of myxomatous degeneration is high, the edge-to-edge technique may not be suitable. Edge-to-edge repairs are also not suitable for many patients, including those with ischemic mitral regurgitation, recurrent mitral regurgitation after complex mitral valve repair, or mitral regurgitation associated with papillary muscle displacement. On the other hand, mitral valve replacement surgeries typically involve open-heart surgery, which can be problematic, especially in an older patient population.

SUMMARY OF EMBODIMENTS OF THE INVENTION

According to some embodiments, a catheter includes a catheter body having a temperature-controlled anchor element thereon that is configured to attach the catheter body to tissue by forming a congealed adherence layer between the anchor element and the tissue. An ablation element is connected to the catheter body and is configured to ablate tissue when the anchor element is attached to the tissue.

In some embodiments, the catheter body includes a first portion having the temperature-controlled anchor element thereon and a second portion having the ablation element thereon. The first and second portions are movable relative to each other. The first portion can be inserted in the second portion and can be movable between an extended position, in which the first portion extends away from the second portion, and a retracted position, in which the first portion is withdrawn into the second portion. The first portion can be configured to be attached to tissue by the anchor element when the first portion is in the extended position, and the second portion can be configured to ablate tissue adjacent the anchor element with the ablation element when the first portion is in the retracted position. In some embodiments, the second portion is inserted in the first portion and is movable between an extended position, in which the second portion extends away from the first portion, and a retracted position, in which the second position is withdrawn into the first portion. The first portion can be configured to be attached to tissue by the anchor element when the second portion is in the retracted position, and the second portion is configured to ablate tissue adjacent the anchor element when the second portion is in the extended position.

In some embodiments, the anchor element is configured to be cooled to a temperature in a range between −90° C. and −30° C.

In some embodiments, the anchor element includes a cryogenically cooled fluid source that is configured to cool at least a portion of the anchor element to form the congealed adherence layer.

In some embodiments, the anchor element is configured to attach the catheter body to tissue when the tissue is moving relative to the catheter body. The tissue can include a mitral valve. The ablation element can be configured to ablate the tissue of the mitral valve when the mitral valve is moving.

In some embodiments, the anchor element is spaced apart from the ablation element such that the anchor element maintains a temperature sufficiently cool to form the congealed adhesion layer and the ablation element maintains a temperature sufficiently to ablate tissue.

In some embodiments according to the invention, methods for ablating tissue include positioning a catheter body having a temperature-controlled anchor element thereon adjacent body tissue. The anchor element is cooled to a temperature sufficient form a congealed adherence layer between the anchor element and the tissue to attach the catheter body to the tissue. An ablation element connected to the catheter body is positioned adjacent the tissue. The tissue is ablated by the ablation element when the anchor element is attached to the tissue.

BRIEF DESCRIPTION OF THE DRAWINGS

The accompanying drawings, which are incorporated in and constitute a part of the specification, illustrate embodiments of the invention and, together with the description, serve to explain principles of the invention.

FIGS. 8a-8b are transthoracic echocardiograms performed before RF ablation (FIG. 8a) and after ablation (FIG. 8b) according to embodiments of the present invention. FIG. 8a-8b illustrate a reduction in mitral valve regurgitation from 59 cc to 33 cc. The anterior mitral valve leaflet received three RF ablations at 12 Watts for 50 seconds.

FIG. 9a illustrates the biaxial response of a healthy ovine mitral valve anterior leaflet. FIG. 9b illustrates the biaxial response of a diseased myxomatous mitral valve leaflet prior to radiofrequency (RF) ablation. FIG. 9c illustrates the circumferential response of the myxomatous mitral valve leaflet after RF ablation at 15 Watts for 15 seconds with an arrow showing the difference due to ablation. FIG. 9d illustrates a radio response of the myxomatous mitral valve leaflet before and after RF ablation with an arrow illustrating the difference due to ablation.

DETAILED DESCRIPTION OF EMBODIMENTS OF THE INVENTION

Figure 1:
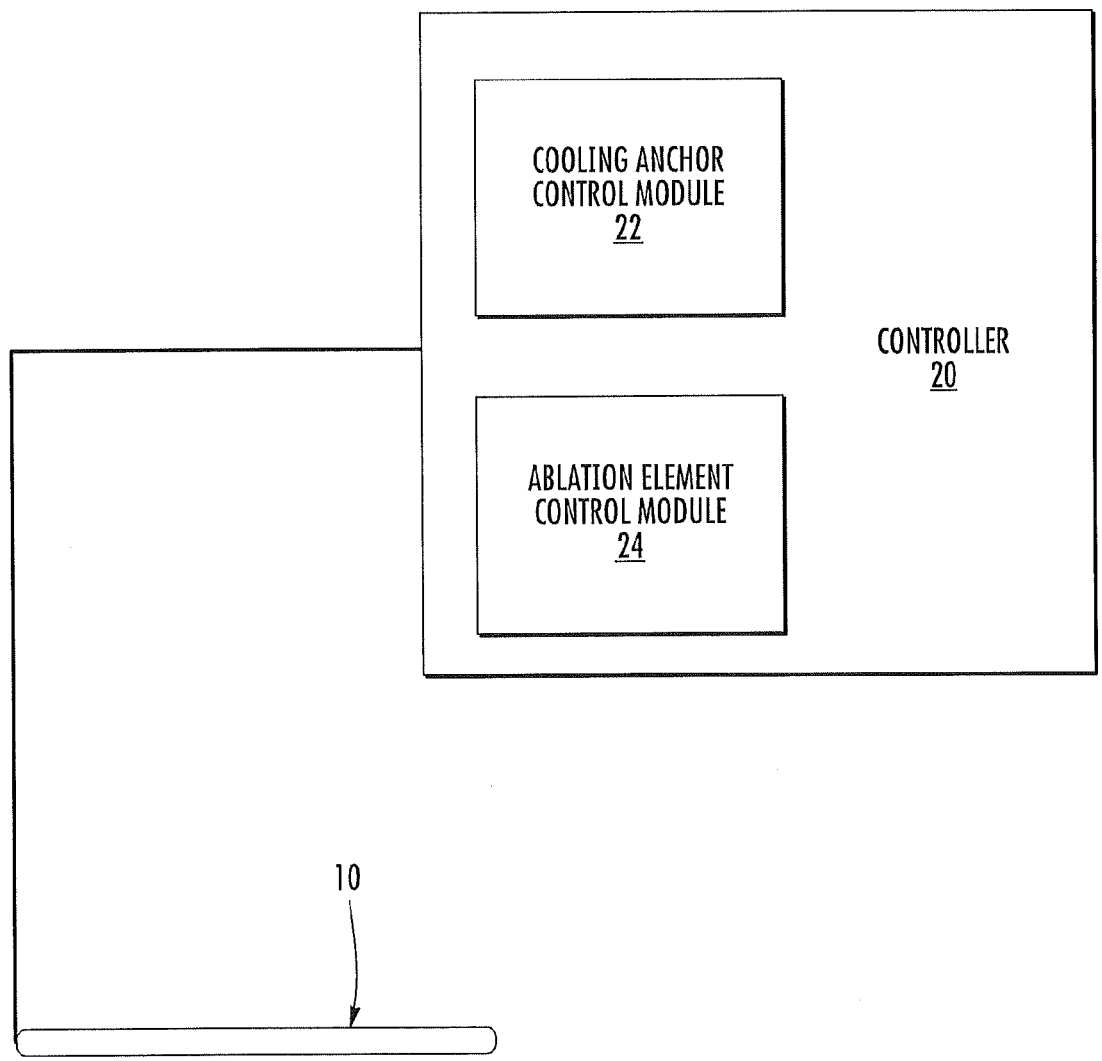
FIG. 1 is a schematic diagram of a controller and a catheter according to some embodiments of the present invention.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, the present invention may be embodied in hardware and/or in software (including firmware, resident software, micro-code, etc.). Furthermore, embodiments of the present invention may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain or store the program for use by or in connection with the instruction execution system, apparatus, or device.

The computer-usable or computer-readable medium may be, for example but not limited to, an electronic, magnetic, optical, electromagnetic, infrared, or semiconductor system, apparatus or device. More specific examples (a non-exhaustive list) of the computer-readable medium would include the following: a portable computer diskette, a random access memory (RAM), a read-only memory (ROM), an erasable programmable read-only memory (EPROM or Flash memory), and a portable compact disc read-only memory (CD-ROM).

As shown in FIG. 1, a catheter 10 according to some embodiments of the present invention is connected to a controller 20. The catheter 10 includes a temperature-controlled anchor element and an ablation element (shown in FIGS. 2-6). The controller 20 includes an anchor control module 22 configured to control the anchor element on the catheter 10 and an ablation control module 24 configured to control the ablation element on the catheter 10.

Figure 2:
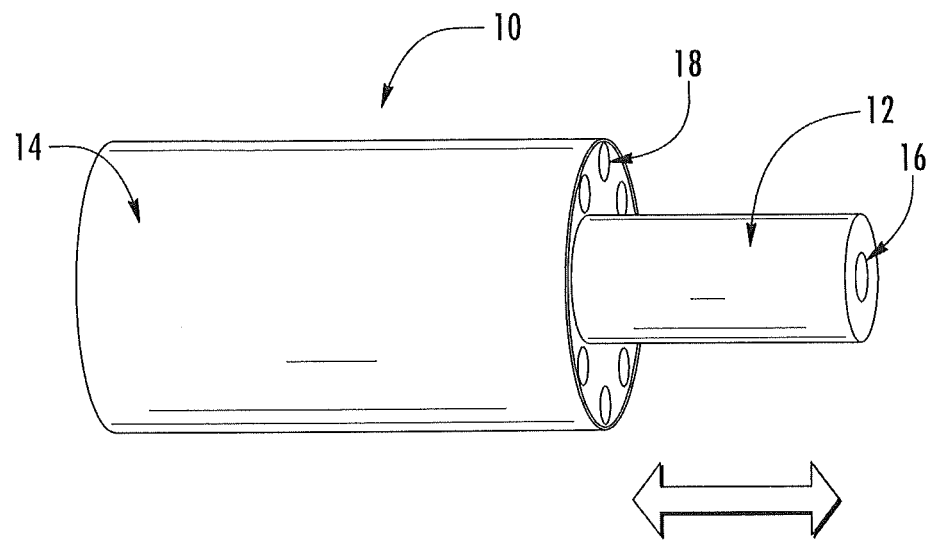
FIG. 2 is a side perspective view of a catheter having a temperature-controlled anchor element according to some embodiments of the present invention.
Figure 3:
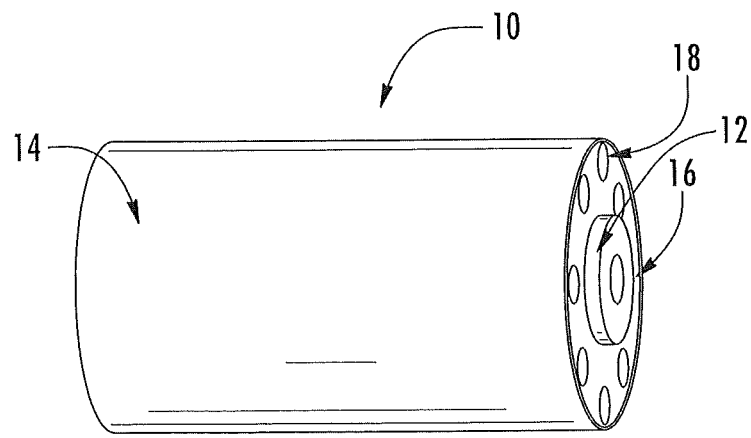
FIG. 3 is a side perspective view of the catheter of FIG. 2 with a portion of the catheter in a retracted position.

As illustrated in FIGS. 2-3, an end of the catheter 10 includes an anchoring portion 12 having a temperature-controlled anchor element 16 thereon, and an ablating portion 14 having ablation elements 18 thereon. The ablation elements 18 can be RF ablation elements; however, any suitable ablation element can be used, including microwave energy, laser energy, heat energy and/or cryogenically cooled ablation elements. The temperature-controlled anchor element 16 can be a cryogenically cooled element.

The portions 12 and 14 of the catheter 10 are movable with respect to one another such that the anchor element 16 can anchor the catheter 10 to a region of tissue when the anchoring portion 12 is in the extended position (shown in FIG. 2). When the anchoring element 16 is successfully anchored to a region of tissue, the anchoring portion 12 and the ablation portion 14 can be moved into the retracted position (shown in FIG. 3) such that the ablation elements 18 are positioned adjacent or in contact with tissue adjacent the anchoring element 16.

The anchoring element 16 can anchor the catheter 10 to tissue using a temperature-controlled surface to form a congealed adhesion layer, such as a solid ice or frozen layer that is formed from tissue and/or fluids adjacent the tissue. In some embodiments, the anchoring element 16 is configured to provide a cryogenically cooled surface at a temperature that is higher that the temperature used to cryogenically ablate tissue, but sufficiently cool so as to form a frozen or congealed adhesion layer to anchor the catheter 10 to the tissue. For example, the anchoring element 16 can include a cooling chamber for receiving an amount of cooling fluid (such as liquid nitrogen), and the amount of cooling fluid and/or temperature of the anchoring element 16 can be controlled by the anchor control module 22 of FIG. 1. The anchoring element 16 can include structures for cooling a catheter surface that are similar to cryogenic catheter ablation tips used to cryogenically ablate tissue, for example, as described in U.S. Pat. No. 7,465,300 to Arless; however, the anchoring element 16 can operate at temperatures that are generally higher than temperatures used for cryogenic ablation. Accordingly, in some embodiments, the anchoring element 16 can be maintained at a temperature that does not cryogenically ablate tissue or change the mechanical properties of the tissue, but is sufficiently cool so as to form an ice or frozen region/adhesion layer for securing the catheter 10 to the tissue.

In some embodiments, the catheter 10 can be used to treat mitral valve diseases or malfunctions. The anchoring element 16 can be sized and configured to attach to at least a portion of the mitral valve of a beating heart, i.e., while the mitral valve is moving with respect to the surrounding cardiac tissue. In some embodiments, the anchor control module 24 of FIG. 1 can include a cardiac cycle monitor that uses the cardiac cycle to estimate the moving location of the mitral valve during a cardiac cycle so that a medical health professional can move the anchoring element 16 into position on the mitral valve. Catheter guidance techniques known to those of skill in the art may also be used.

The anchoring element 16 can connect the anchoring portion 12 of the catheter to the mitral valve of a beating heart such that the anchoring portion 12 moves together with the mitral valve, and the ablating portion 14 can be positioned adjacent the mitral valve tissue while the mitral valve continues to function during the cardiac cycle. Thus, ablation of a portion of the mitral valve can be performed percutaneously while the mitral valve is moving with respect to the surrounding cardiac tissue during the cardiac cycle without substantial disruption to cardiac function. Without wishing to be bound by any particular theory, the ablation element 18 can deliver ablation energy, such as RF energy, such that the collagen of at least a portion of the mitral valve (e.g., at least one leaflet) coagulates. The coagulated collagen can alter the intrinsic stiffness of the mitral valve, and consequently, improve cardiac function without requiring invasive surgeries for mitral valve repair or replacement.

Figure 4:
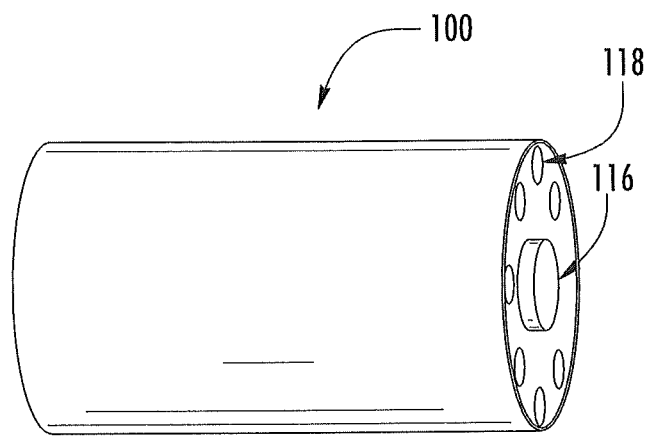
FIG. 4 is a side perspective view of another catheter having a temperature-controlled anchor element according to some embodiments of the present invention.
Figure 5:
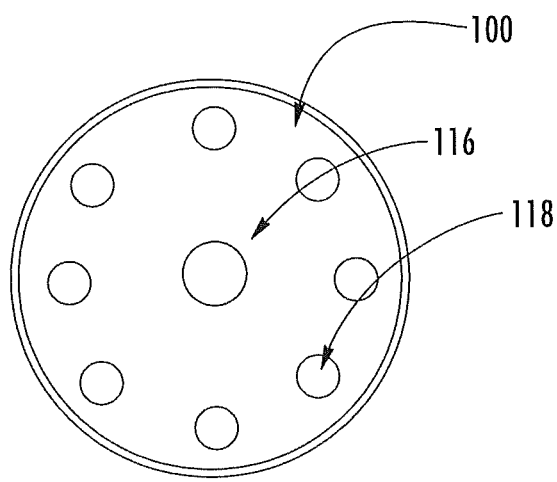
FIG. 5 is a front view of the catheter of FIG. 4.
Figure 6:
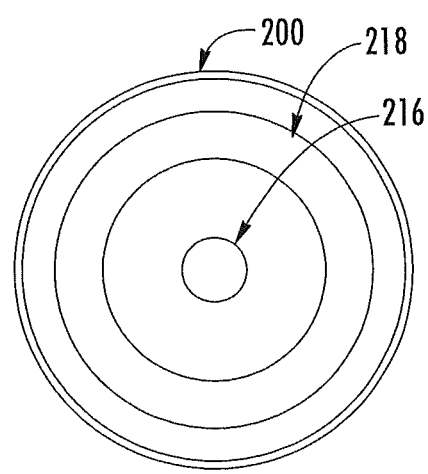
FIG. 6 is a front view of another catheter having a temperature-controlled anchor element according to some embodiments of the present invention.

Although embodiments of the catheter 10 in FIGS. 2-3 illustrate a coaxial configuration between an anchoring portion 12 and an ablating portion 14, it should be understood that other catheter configurations can be used. In some embodiments, the portions 12, 14 could be provided in a side-by-side configuration and held together in a catheter sheath. Moreover, the positions of the anchoring element 16 and the ablation elements 18 could be reversed and/or any number of elements 16, 18 can be used. Thus, various catheter configurations, including the number and placement of anchoring and ablating elements, are within the scope of the current invention. For example, in some embodiments as shown in FIGS. 4-5, a catheter 100 includes a single tip having the anchoring element 116 and ablating elements 118 thereon. As shown in FIG. 6, a catheter 200 includes a central anchoring element 216 and a ring electrode ablation element 218.

Figure 7:
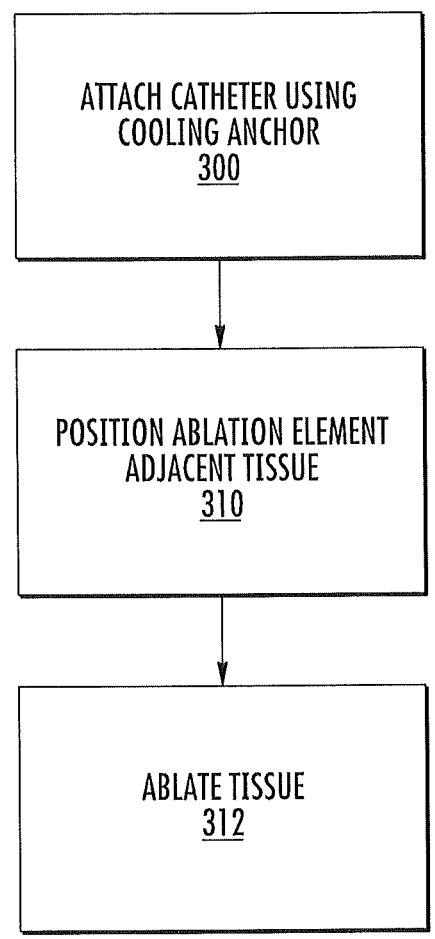
FIG. 7 is a flowchart illustrating operations according to some embodiments of the present invention.

As shown in FIG. 7, a catheter (such as the catheters 10, 100, 200 illustrated in FIGS. 2-6) can be attached to tissue using a cooling anchor (Block 300). An ablation element is positioned adjacent the tissue (Block 310). The tissue is ablated while the catheter is anchored to the tissue by the cooling anchor (Block 312).

Embodiments according to the present invention will now be described with respect to the following non-limiting examples.

EXAMPLE

Three beagles were found to have mitral valve prolapse causing severe mitral valve regurgitation with a mean ejection fraction of 66±3%. These canines underwent a right lateral thoracotomy and the mitral valve was exposed by opening the left atrium and radio frequency (RF) ablation was applied to the prolapsed leaflets of the mitral valve. Mitral regurgitation volume was calculated using a proximal isovelocity surface area method on pre- and post-ablation echocardiograms. Each leaflet was treated with an average of 3 applications of RF ablation using a mean power of 15±2 Watts for a duration of 43±7 seconds. Echocardiography results (FIGS. 8a-8b) revealed that ablation of the prolapsed mitral valve leaflets reduced mitral valve regurgiation by 67±12% (Table 1), which is a change from severe to mild mitral valve regurgitation.

a patient undergoing mitral valve repair due to significant mitral valve regurgitation. The tissue was extremely thick (~5 mm) and myxomatous and when exposed to biaxial planar tension to 60 kPa, the leaflet demonstrated a pathologic, isotropic response with no evident collagen architecture dictating mechanics (FIG. 9b). The leaflet was then subjected to RF ablation at 15 W for 15 s and was then tested again for biaxial compliance. Results revealed that ablation treatment decreased the circumferential stretch of the leaflet by 25% at 60 kPa (FIG. 9c, arrow points from before to after ablation) and increased radial stretch by 21% at 60 kPa (FIG. 9d). When comparing the ablated data lines from FIG. 9c-d, the data appear more similar to the biaxial response of a native, healthy mitral valve (FIG. 9a) with the circumferential direction stiffer than the radial direction, demonstrating the efficacy of RF ablation to acutely alter the mechanical properties of myxomatous mitral valve leaflets.

Preliminary findings therefore suggest that RF ablation of myxomatous or prolapsed mitral valve leaflets leading to severe mitral valve regurgitation will acutely counteract the deleterious nature of the disease. Moreover, this treatment strategy alters the intrinsic mechanical properties of the leaflet and further promotes fibrosis of the leaflet such that future mitral valve regurgitation and subsequent interventions may be reduced or avoided.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:
1. A catheter system comprising:
 a catheter comprising:
  a catheter body having a temperature-controlled anchor element thereon that is configured to attach the cath-

TABLE 1

Echocardiography findings in three beagles with severe mitral valve regurgitation before and after RF ablation

|  | EF (%) | Prolapsed Leaflets | MR | Pre-Ablation MR Vol (cc) | Post-Ablation MR Vol (cc) | % Change in MR Post-Ablation | Ablations | Ablation Power (W) | Ablation Time (s) |
|---|---|---|---|---|---|---|---|---|---|
| Canine 7522 | 72 | Anterior | Severe | 59 | 33 | −44 | 3 | 12 | 50 |
| Canine 6544 | 65 | Posterior | Severe | 230 | 39 | −83 | 3 | 17 | 50 |
| Canine 0692 | 62 | Bileaflet | Severe | 153 | 40 | −74 | 6 | 17 | 29 |
| Mean ± SEM | 66 ± 3 |  |  | 147 ± 49 | 37 ± 2 | −67 ± 12 |  | 15 ± 2 | 43 ± 7 |

Ex Vivo Data

Figure 9A:
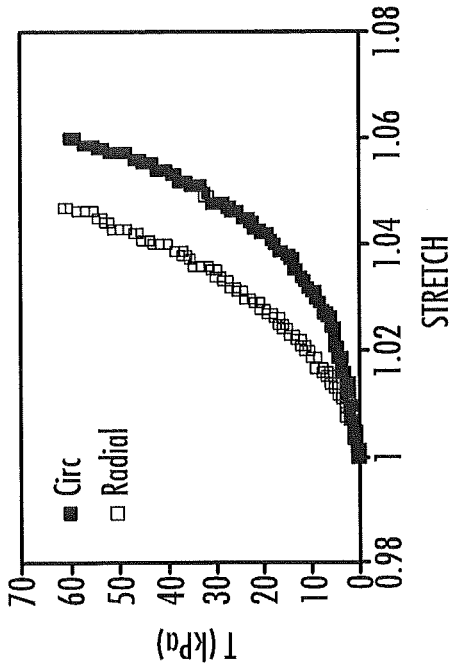
FIGS. 9a-9d are graphs of the stretch (U) verses the tension (T) for mitral valve leaflets.
Figure 9B:
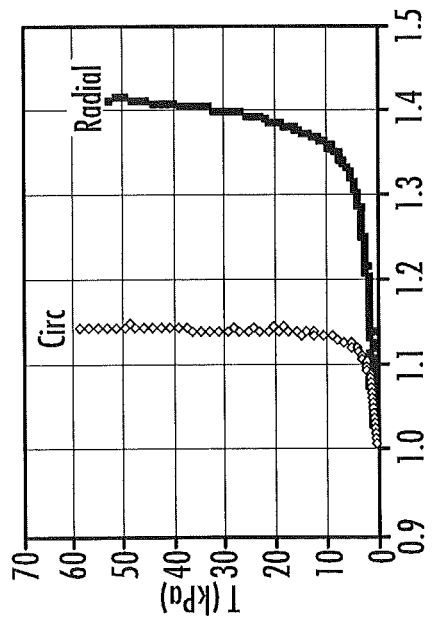
Figure 9C:
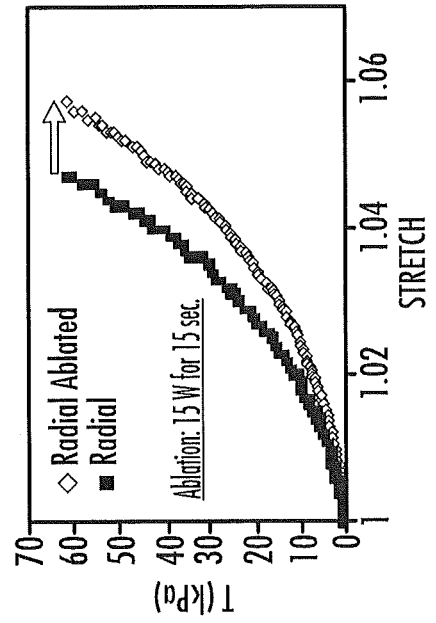
Figure 9D:
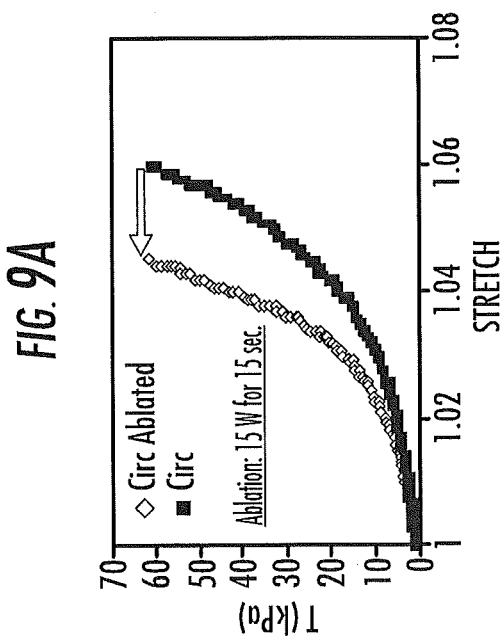

The planar biaxial mechanical response of healthy mitral valve leaflets demonstrates a highly anisotropic response with the circumferential direction being much stiffer than the radial direction (FIG. 9a). This response is due the circumferentially-oriented type I collagen. Previously, a large portion of a myxomatous mitral valve leaflet was obtained from eter body to tissue by forming a congealed adherence layer between the anchor element and the tissue; and
 an ablation element connected to the catheter body and configured to ablate tissue when the anchor element is attached to the tissue; and
a catheter controller comprising a cardiac cycle monitor that uses the cardiac cycle to estimate the moving location of the mitral valve during a cardiac cycle for positioning the temperature-controlled anchor element into a position on the mitral valve.

2. The catheter system of claim 1, wherein the catheter body comprises a first portion having the temperature-controlled anchor element thereon and a second portion having the ablation element thereon, the first and second portions being movable relative to each other.

3. The catheter system of claim 2, wherein the first portion is inserted in the second portion and is movable between an extended position, in which the first portion extends away from the second portion, and a retracted position, in which the first portion is withdrawn into the second portion.

4. The catheter system of claim 3, wherein the first portion is configured to be attached to tissue by the anchor element when the first portion is in the extended position, and the second portion is configured to ablate tissue adjacent the anchor element with the ablation element when the first portion is in the retracted position.

5. The catheter system of claim 1, wherein the second portion is inserted in the first portion and is movable between an extended position in which the second portion extends away from the first portion and a retracted position in which the second position is withdrawn into the first portion.

6. The catheter system of claim 5, wherein the first portion is configured to be attached to tissue by the anchor element when the second portion is in the retracted position, and the second portion is configured to ablate tissue adjacent the anchor element when the second portion is in the extended position.

7. The catheter system of claim 1, wherein the anchor element is configured to be cooled to a temperature in a range between −90° C. and −30° C.

8. The catheter system of claim 1, wherein the anchor element comprises a cryogenically cooled fluid source that is configured to cool at least a portion of the anchor element.

9. The catheter system of claim 1, wherein the anchor element is configured to attach the catheter body to tissue when the tissue is moving relative to the catheter body.

10. The catheter system of claim 9, wherein the tissue comprises a mitral valve.

11. The catheter system of claim 10, wherein the ablation element is configured to ablate the tissue of the mitral valve when the mitral valve is moving.

12. The catheter system of claim 1, wherein the anchor element is spaced apart from the ablation element such that the anchor element maintains a temperature sufficiently cool to form the congealed adhesion layer and the ablation element maintains a temperature sufficiently to ablate tissue.

13. A method for ablating tissue, the method comprising:
monitoring the cardiac cycle with a cardiac cycle monitor that uses the cardiac cycle to estimate the moving location of the mitral valve during a cardiac cycle;
positioning a catheter body having a temperature-controlled anchor element thereon adjacent body tissue comprising mitral valve tissue based on the moving location of the mitral valve while cooling the anchor element to a temperature sufficient to form a congealed adherence layer between the anchor element and the tissue to attach the catheter body to the tissue;
positioning an ablation element connected to the catheter body adjacent the tissue; and
ablating the tissue when the anchor element is attached to the tissue.

14. The method of claim 13, wherein the catheter is attached to the mitral valve in vivo when the mitral valve is moving.

\* \* \* \* \*